United States Patent [19]

Crumpler et al.

[11] Patent Number: 5,664,207
[45] Date of Patent: Sep. 2, 1997

[54] SYSTEMS AND METHODS FOR AUTOMATICALLY SHARING INFORMATION AMONG REMOTE/MOBILE NODES

[75] Inventors: Dennis M. Crumpler; Robert B. Estes, both of Atlanta; Kirby Bryan Jackson, Jr., Decatur, all of Ga.

[73] Assignee: XcelleNet, Inc., Atlanta, Ga.

[21] Appl. No.: 358,106

[22] Filed: Dec. 16, 1994

[51] Int. Cl.$^6$ ................................................ G06F 17/30
[52] U.S. Cl. ...................... 395/766; 345/329; 345/331; 395/610; 705/3
[58] Field of Search ........................... 395/600, 610, 395/617, 209, 216, 221, 331, 332, 202, 203, 608, 609, 200.03, 200.19, 200.02, 200.08, 766, 767, 768, 770

[56] References Cited

U.S. PATENT DOCUMENTS

| | | | |
|---|---|---|---|
| 5,077,666 | 12/1991 | Brimm et al. | 364/413.02 |
| 5,319,543 | 6/1994 | Wilhelm | 364/401 |
| 5,493,692 | 2/1996 | Theimer et al. | 455/26.1 |
| 5,495,610 | 2/1996 | Shing et al. | 395/600 |
| 5,513,126 | 4/1996 | Harkins et al. | 364/514 A |

FOREIGN PATENT DOCUMENTS

| | | |
|---|---|---|
| 0 565 314 A2 | 10/1993 | European Pat. Off. . |
| WO91/01022 | 1/1991 | WIPO . |
| WO92/22033 | 12/1992 | WIPO . |

OTHER PUBLICATIONS

RemoteWare SERVER Operations Guide, XcelleNet, Inc., Software Release 1.4 Dec. 1992.
RemoteWare SERVER Setup Guide, Xcellenet, Inc., Software Release 1.4 Dec. 1992.
Micrpsoft Press Computer Dictionary, Second Edition, Microsoft Press Jun. 1994.
*RemoteWare FORMS and RemoteWare QUERY Reference Manual*, Software Release 1.3, XcelleNet, Inc., 1993.
PCT Search Report, PCT/US95/14493, Jun. 11, 1996.

Primary Examiner—Thomas G. Black
Assistant Examiner—Hosain T. Alam
Attorney, Agent, or Firm—Bell, Seltzer, Park & Gibson, P.A.

[57] ABSTRACT

Information is automatically shared among a plurality of remote/mobile data processing nodes which are temporarily and intermittently linked to a data processing server by distributing an information form to users corresponding to first remote/mobile nodes. A user may complete the form to create an instance of the form and define an instance distribution list. The instance is automatically distributed to users corresponding to the distribution list. As owner of the form, the user may also modify the form, and these modifications are also automatically distributed to the users at the third node. A second form may be linked to the form and automatically distributed to the third nodes as well. When distributing a file to a node, any other files which are required are also automatically distributed.

42 Claims, 12 Drawing Sheets

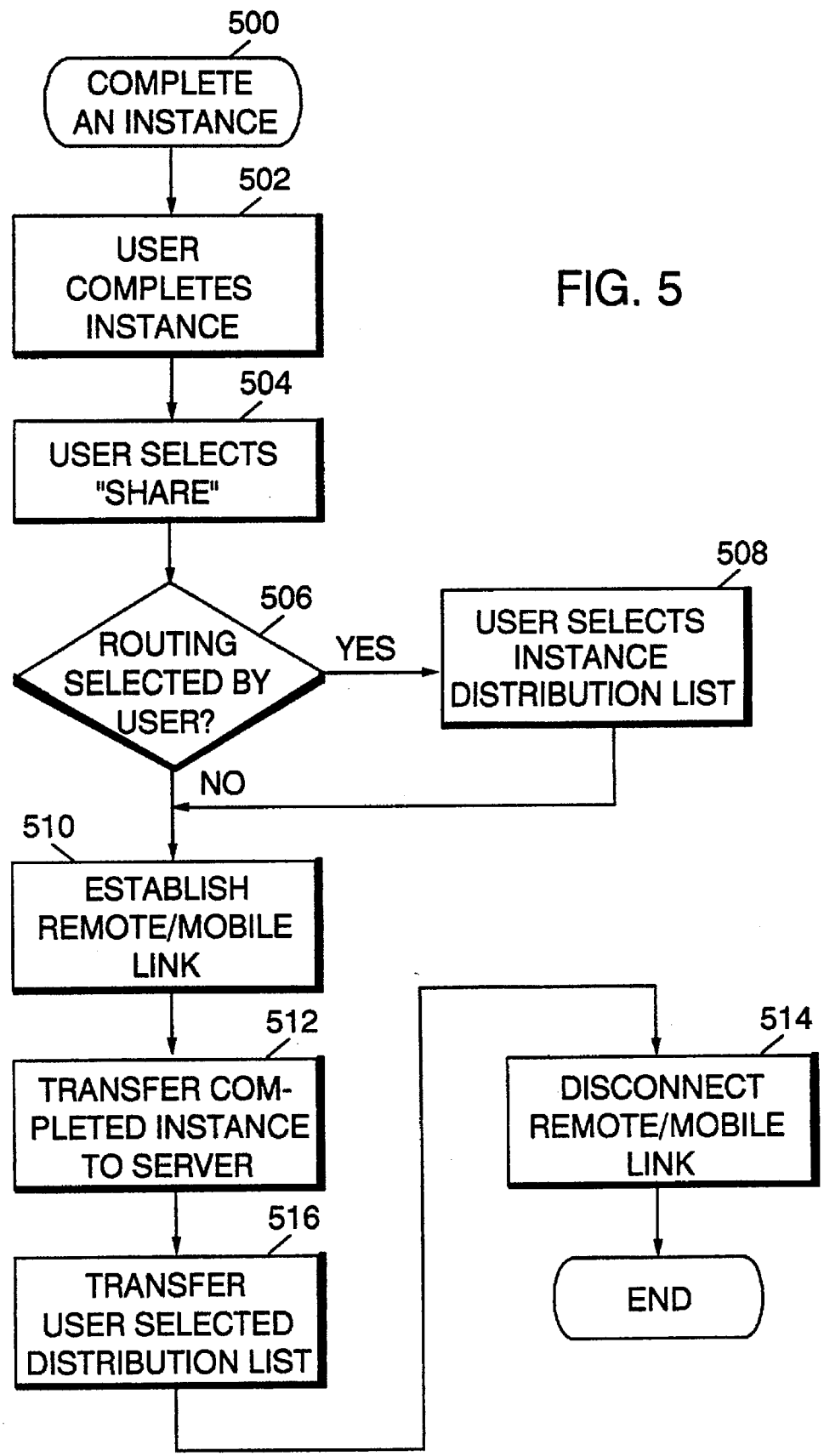

FIG. 10

```
Patient  Edit  Table  Communications  Help
┌─────────────────────────────────────────────────┐
│ HBO&Company          Patient Profile & Action Form │
│ [=][+][-][▽][△][✓][✗]                            │
│                                                   │
│              Patient Information                  │
│ Patient                    Gender                 │
│ HIN  152-46-2589 ▽         ○ Male  ○ Female       │
│ Last  Petersen  First Debra M    Access to Records│
│ Date Born 12/12/67  T            ⊙ Complete ○ Restricted│
│                                  Patients Primary Physician│
│                                  Dr. McCall       │
│                                  Patient Address  │
│                                  4512 Morningside │
│                                  Atlanta, Ga, 30308│
│                                  Telephone        │
│                                  (404) 222-2222   │
│                                                   │
│              Encounter Information                │
│ Action Required            Action Records         │
│ ☒ Get Medical &            Referral Information   │
│   Insurance History        Appointment Information│
│                            Encounter Information  │
│ ☒ Record                   Patient Records        │
│   Encounter Info.          Patient Medical History│
│                            Insurance Information  │
│                                                   │
│                            Other Information/Notes│
│                            ┌──────────────────┐   │
│                            │◁                ▷│   │
│                            └──────────────────┘   │
│                                                   │
│ Ready            Patient 1 of 1    Successful Session 12/1 09.45.14│
└─────────────────────────────────────────────────┘
```

FIG. 11

CURRENT ENCOUNTER

☒ Time In  12 01/94  09 46  AM      ☒ Time Out  12 01/94  09 46  AM

Reason for Visit

○ Acute Complaint
○ Follow-up of Acute Condition
○ Referral for Specific Service
○ Work_Up/Care of Undiagnosed Complaint
○ Preventative/Rehabilitation Service
● Care of Established Chronic Condition
○ Routine Health Evaluation
○ Other Current Diagnosis

| ICD-9-CM | Description | Certainty | |
|---|---|---|---|
| 34C | CTS | 3 | ▷ |
| | | | ▷ |
| | | | ▷ |
| | | | ▷ |
| | | | ▷ |

Date of Last Action  11/11/92

☒ Current Action(s)
☐ Evaluation of Diag./Status
☒ Preventative/Therapeutic Rehabilitative Intervention(s)
☐ Counselling/Education
☐ Other Diagnosis Specific Action

[ Procedure ]   [ Medication ]   [ Follow-Up ]

SYSTEMS AND METHODS FOR AUTOMATICALLY SHARING INFORMATION AMONG REMOTE/MOBILE NODES

FIELD OF THE INVENTION

This invention relates to data processing systems and methods and more particularly to systems and methods for linking a plurality of data processing systems for communication therebetween.

BACKGROUND OF THE INVENTION

Since the early days of computing, data processing systems have been linked to users via communications networks. Initially, a host or mainframe computer was linked to user terminals. With the advent of the personal computer, "intelligent workstations" have been linked to host computers.

As more and more computing systems have become personal computer based, personal computers have been linked into Local Area Networks (LAN) which are managed by a server to provide client/server applications. These client/server networks can also be linked to mainframe and other computers.

Traditional LAN-based client/server networks, and most other computer networks, assume a near-ideal operating environment. In particular, LANs assume continuously connected users who are computer literate. Since the LAN connections between computers are hard wired, error-free reliable connections are assumed. Thus, the LAN-based client/server environment allows knowledge-workers and PC professionals to operate in a near ideal environment.

Unfortunately, traditional LAN-based client/server networks poorly serve the needs of important classes of users, referred to herein as "remote/mobile" users. As used herein, "remote/mobile" means "temporarily and intermittently linked", wherein temporarily means "lasting for a limited time" and intermittently means "coming and going at intervals, not continuous, or occasional". An example of remote/mobile users is point-of-sale terminals in a chain of, for example, 5,000 retail stores, where each point-of-sale terminal needs to connect to the headquarters central computer for short periods of time for communication therebetween, rather than continuously. Another example of remote/mobile users is a mobile sales force which typically uses laptop computers and connects with the home office for short periods of time from various locations, such as hotels, customer sites or cars.

Users of remote/mobile computers, such as laptop and notebook computers, point-of-sale systems, personal computers, personal digital assistants and the like are typically "transactional" workers rather than knowledge workers, and are not typically PC literate. They need to link to a central office on a temporary and intermittent basis to obtain information from the central office or to transfer information to the central office. The connections between the remote/mobile node and the data processing server may use switched wire or wireless connections. Accordingly, communications tend to be slow and unreliable.

Traditional LAN-based client/server systems have attempted to meet the needs of remote/mobile users by allowing remote dial-in to the LAN. However, remote dial-in has heretofore worked effectively only for small numbers of remote/mobile users, and has used a LAN-based paradigm which is not amenable to the unique requirements of the remote/mobile user.

A major breakthrough in remote/mobile computing was provided with the introduction of RemoteWear versions 1.0–1.4 by XcelleNet, Inc., Atlanta, Ga., assignee of the present invention. The RemoteWare systems provided a communication model which was specifically geared to remote/mobile environments. One or more RemoteWare servers can be connected to a LAN to control the exchange of information between a central site and hundreds or thousands of remote/mobile computers and their users and applications. The RemoteWare server provides information management, resource management, scheduling, communication services, information monitoring and control services needed by large numbers of remote/mobile users who are temporarily and intermittently linked to the remote/mobile network.

Communications between the server and the remote/mobile nodes are designed to keep connect time at a minimum. Thus, the connection cost is minimized and the time that the transactional worker needs to spend connected to the central system are minimized. Moreover, the system is designed to support low bandwidth and unreliable connections.

RemoteWare Versions 1.0–1.4 include an application which provides a remote transactional management system. The remote transactional management system, designated as "RemoteWare FORMS" includes a forms editor which is used to create forms with graphics, fields, text and bitmaps. Once completed, the form becomes an application that can be assigned to a remote/mobile users desktop. Once the form is assigned to a user's desktop, the system sends the form to the users to whom that user desktop is assigned. A forms node program displays the form at the node. The node user enters the required information on the form. The node user then posts the completed form which is automatically sent to the RemoteWare server. If routing has been enabled for the form, the user may forward a data set to another user and sends copies to others via a messaging service. The data may be viewed in the context of the form in which it was entered, and may be printed. The RemoteWare FORMS system is described in a publication entitled *"RemoteWare FORMS and RemoteWare QUERY Reference Manual, Software Release 1.3"*, Copyright 1993, XcelleNet, Inc.

Notwithstanding the ability to create and route forms to remote/mobile users which was provided with the introduction of RemoteWare Version 1.0–1.4, there continues to be a need to provide improved methods and systems for automatically sharing information among users of remote/mobile computers.

SUMMARY OF THE INVENTION

The invention provides methods and systems for automatically sharing information among remote/mobile users. Many business processes require automatic sharing of information among large numbers of remote/mobile users. For example, a remote/mobile sales or service force may need access to a customer profile for a particular customer. The customer profile may need to be updated with address changes and other changes, and these updates need to be automatically distributed to users who routinely need to be made aware of these changes. Moreover, sales and service call records to a customer may need to be automatically distributed to select members of the sales force to update their knowledge of a particular customer or group of customers.

According to the invention, information is automatically shared among a plurality of remote/mobile data processing nodes which are temporarily and intermittently linked to a data processing server by designing an information form and placing the information form on the server. The form is identified as being shareable, and an associated form distribution list is assigned to the form in order to identify users corresponding to first remote/mobile nodes. Remote/mobile communication links are established to the first remote/mobile nodes, and the form is transferred to the first remote/mobile nodes. The remote/mobile communications links are then disconnected from the first remote/mobile nodes.

An instance of the form is created at a second selected one of the first nodes by a user. An instance of a form is a form into which information or data has been entered. For example, if the form is a customer profile form, a user creates a customer profile for a particular customer. An instance distribution list is also assigned to the instance of the form in order to identify users corresponding to third remote/mobile nodes who need or may want to see copies. In the customer example described above, these users may be those sales force members who will interact with that customer. The instance distribution list may be established by the user of the second node. Alternatively, it may be established at the server. A remote/mobile communication link is then established between the second node and the server and the instance of the form is transferred to the server, along with the instance distribution list. The remote/mobile communications link is then disconnected between the second node and the server.

In response to receipt of the instance of the form from the second node, remote/mobile communications links are automatically established between the server and the third remote/mobile nodes. A copy of the instance of the form is transferred from the server to the third remote/mobile nodes and the remote/mobile communications links are then disconnected. The distributed instance appears in the recipient's in-box and is displayed upon selection. Accordingly, a copy of the instance of the form is automatically distributed to all remote/mobile users who have a need to know of the information contained in the instance of the form and who are in the distribution lists as assigned by the form's instance creator. Multiple instances of the form may be created by multiple users, and each instance is distributed to the appropriate remote/mobile users. Automatic sharing of information is thereby provided.

According to another aspect of the invention, the originator of an instance of a form is the owner of that instance. As such, only the owner of the instance can update or modify the data contained therein. Thus, in the example described above, the user at the second node is the owner of the instance of the form. Only the user at the second node can update the instance of the form. When updating the instance of the form, the updates are automatically distributed to the third remote/mobile nodes, without the need for action by the owner. Updating of information in an instance of a form by remote/mobile users other than the owner is prevented. Once updated, only the updates are automatically sent to the server and automatically distributed to the third remote/mobile nodes. Upon receipt, the updates automatically replace the original data elements. The updates may be highlighted in the instance form, for example, using bold or color fields. An indication is also placed in the recipients in-box that the instance has been changed.

According to another aspect of the invention, forms maybe linked for automatic sharing of information. A second information form is created and placed on the server. The second information form is linked to the information form described above, now referred to as the first information form or first form, so that an instance of the second form may be automatically launched while viewing the instance of the first information form. In the sales force example described above, the linked form may be a "customer call" form which documents the results of a customer call for a particular customer. The customer call form is linked to the customer profile form so that customer call information may be distributed while viewing the customer profile form. The form distribution list is automatically assigned to the second form so that the linked form is automatically distributed to the first remote/mobile nodes. Remote/mobile communications links are again established to the first remote/mobile nodes. The second form is transferred to the first nodes and the remote/mobile communications links are disconnected.

A user at a fourth one of the first remote/mobile nodes launches an instance of the second form while viewing an instance of the first form. The fourth node typically is not the same as the second node, but it may be the same node. The instance distribution list of the instance of the first form is assigned to the instance of the second form so that the linked instance form is automatically distributed to the recipients of the instance of the original form (i.e. to the third remote/mobile nodes). Remote/mobile communications links are then established between the fourth node and server, and the instance of the second form is transferred to the server. The remote/mobile communications links are then disconnected. Upon receipt at the server, remote/mobile communications links are established between the server and the third remote/mobile nodes. The instance of the second form is transferred from the server to the third remote/mobile nodes and the remote/mobile communications links are disconnected.

The above-described concept of ownership also applies to the linked form. Thus, the instance of the linked form can only be modified by the owner (fourth node). Upon modification by the owner, the modifications are automatically distributed to the third remote/mobile nodes.

Accordingly, information is automatically shared between groups of users in a remote/mobile communications network. Forms and linked forms are automatically distributed to all users who might desire to create an instance of the form. Upon creation of an instance of a form, a distribution list is set up and the instance is automatically distributed. Subsequent updates of the instance, which are permitted only by the owner (originator) of the instance, will automatically be distributed to recipients of the original instance. Instances of linked forms will also be automatically distributed to the same distribution list as the instance of the original form from which the linked form was launched. Updates of the instance of the linked form, which may only be created by the owner of the instance of the linked form, will also be automatically distributed to the same set of recipients. From the user perspective, the user may create an instance of a form and be assured that the instance will be shared with all other relevant users and that updates will also be shared with all relevant users. Automatic sharing of information is thereby provided.

According to another aspect of the invention, a probe of a node is initiated prior to transferring a form or an instance of a form to the node, in order to insure distribution of information efficiently. In particular, in order to effectively utilize a form, other required information and/or software may need to reside at the user's node. For example, a form may require a database or spreadsheet program to relate fields in the form to one another. In order for the user to use the form, the underlying database or spreadsheet program may need to reside at the node.

Accordingly, prior to transferring a form or an instance of a form to a node, a "probe" may be initiated of the node. The probe will determine whether required files exist at the node. If not, the required files are transferred to the node during a remote/mobile communication to the node. The instance is not transferred until it is ascertained that the correct files reside at the node.

A probe is also used to determine whether all the information necessary is resident at a node. For example, if an instance of a linked form is distributed to a node, a probe is used to verify that the linked instance of the original form is also present at the node. If not, the original instance is also distributed to the node. Accordingly, all file transfers will be accompanied by other files which are required for use with the transferred file, if the other files are not already present at the node. Transfers of files which cannot be used or which are not truly needed are thereby reduced or eliminated. The probe technique can be used prior to any file transfer between the server and a node, in order to ensure that all required files are present at the node.

BRIEF DESCRIPTION OF THE DRAWINGS

FIG. 5 is a flowchart illustrating operations for completing an instance according to the present invention.

FIG. 10 illustrates an example of a form according to the present invention.

FIG. 11 illustrates a linked form according to the present invention.

DETAILED DESCRIPTION OF PREFERRED EMBODIMENTS

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
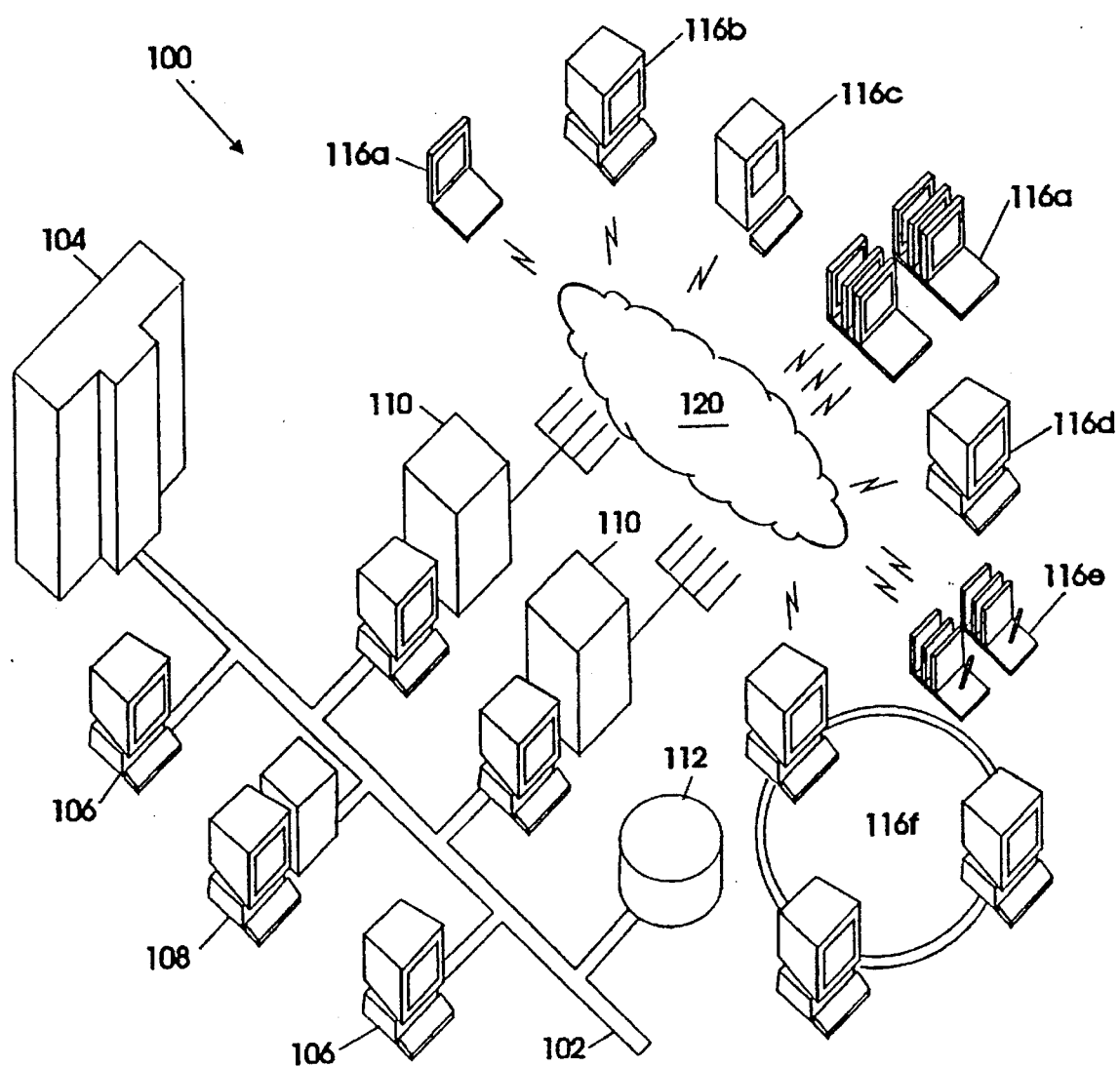
FIG. 1 is a block diagram of a known remote/mobile communications system with which the present invention may be used.

Referring now to FIG. 1, a remote/mobile communication system in which the present invention may be practiced is illustrated. As shown in FIG. 1, remote/mobile communication system 100 includes a local area network (LAN) 102. Mainframe computer 104, LAN workstations 106, a LAN file server 108 and a LAN database 112 are provided and interconnected in a manner well known to those having skill in the art.

In order to provide remote/mobile communications, one or more remote/mobile servers 110 are attached to the LAN 102. Each remote/mobile server may be a personal computer running in the OS/2 operating environment and which runs RemoteWare Versions 1.0–1.4 marketed by the assignee of the present invention. RemoteWare Versions 1.0–1.4 act as the control point for information management, providing the resource management, scheduling, communication services, information monitoring and control services needed by the remote/mobile network. RemoteWare Version 1.4 is described in a manual entitled *"RemoteWare SERVER Operations Guide, Software Release 1.4"*, Copyright 1992, XcelleNet, Inc., the disclosure of which is hereby incorporated herein by reference.

Remote/mobile servers 110 are linked to a remote/mobile communications network 120. Remote/mobile communications network 120 includes various wire line connections such as switched analog, ISDN, and X.25 or wireless connections such as switched and digital cellular, satellite and radio frequency. Although leased lines and other permanent communication lines may also be used, these are not preferred due to their high cost.

A large number (typically hundreds or thousands) of remote/mobile data processing nodes 116a–116f are connected to remote/mobile communications network 120. Each remote/mobile data processing node, also referred to herein as a "node" includes a data processing unit which is temporarily and intermittently linked to server 110. Nodes 116 may include laptop computers 116a, personal computers 116b, MacIntosh computers 116c, point-of-sale systems 116d, pen-based systems 116e and other remote LANs 116f. It will be understood by those having skill in the art that remote/mobile data processing nodes 116 may include any microprocessor driven units such as cellular telephones, personal digital assistants and other workstations and terminals. Each node 116 preferably runs a node software program in background, and which operates in conjunction with the remote/mobile server 110. The node software initiates or responds to communications sessions, supports interactive remote console sessions, relays node status information to the server 110, and relays command line level instructions to the node operating system. An example of node software is RemoteWare Node Version 1.4, marketed by the assignee of the present application. RemoteWare Node Version 1.4 is described in a publication entitled *"RemoteWare SERVER Setup Guide, Software Release 1.4"*, Copyright 1992, XcelleNet, Inc., the disclosure of which is hereby incorporated herein by reference.

As already described, the remote/mobile communication system is designed to reduce connect time. By reducing connect time, the costs of the physical network, such as a cellular phone network or a long distance phone line network, are minimized. Moreover, the amount of time that a node (and an end user operating the node) needs to be on line is reduced. Finally, error free connections are provided, notwithstanding the inherent unreliability of the communications links.

Figure 2:
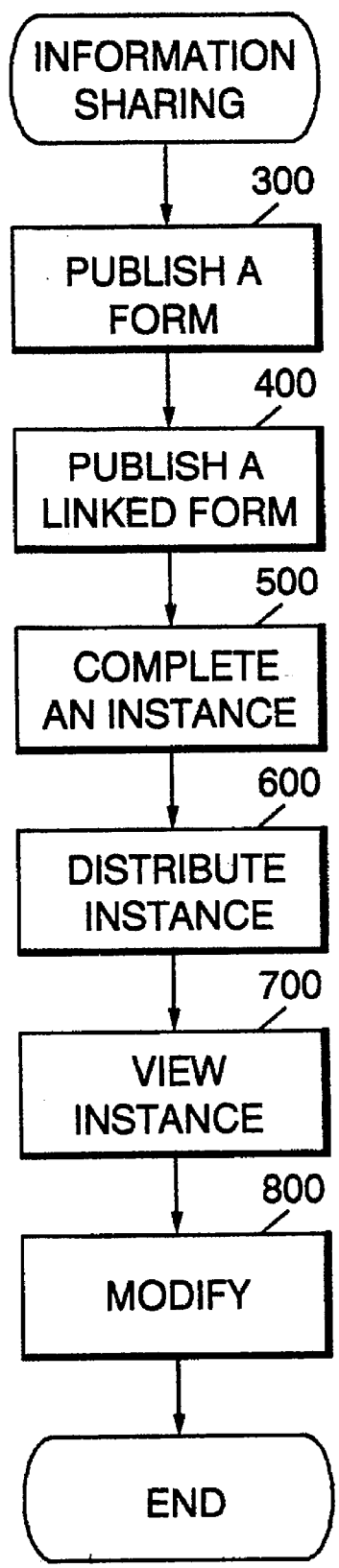
FIG. 2 is a flowchart illustrating overall operations for information sharing according to the present invention.

Referring now to FIG. 2, operations for automatic information sharing among remote/mobile nodes will now be described. In general, information sharing begins by "publishing" a form at Block 300. A form is first designed for use by remote/mobile users. FIG. 10 illustrates an example of a Patient Profile & Action Form. This form may be used by a health care provider such as an HMO or a PPO. The HMO may distribute this form to the hospitals or clinics in its group. The form is published by assigning the form to a form distribution list, and automatically distributing the form to first remote/mobile nodes corresponding to the distribution list.

Similar operations may be performed for a linked form at Block 400. A linked form differs from that of the form described above, now referred to as the first form, because the linked form shares information from the original form. The linked form uses the same distribution list as the first form, so that it is also automatically distributed to the first nodes. FIG. 11 is an example of a Current Encounter Form which is linked to the form of FIG. 10.

Still referring to FIG. 2, at Block 500 a receiver of a form, for example a user at a second node selected from the first nodes, may produce an instance of a form by entering data into the form. The originator of the instance becomes the owner of the instance. In the Example of FIG. 10, the owner of the form, and of instances of the form, may be the "Patient Records" department of the HMO. A new instance is created for each new patient. The instance is distributed to all health professionals in the HMO group who might deal with the patient. The linked form of FIG. 10 details a patient encounter. Each time the patient is "encountered" the health worker selects "Encounter Information" on the form of FIG. 10 to launch the linked form of FIG. 11 which is completed and shared. There can be, and usually are, several Current Encounter forms for each patient.

At Block 600, the instance is distributed to users on an instance distribution list, which identifies users at third nodes selected from the first nodes. The instance distribution list may be set up by the user at the second node or by the system administrator at the server. After distribution, a recipient of the instance may view the instance at Block 700.

Instances may be modified by the owner at Block 800. Only the owner can modify the instance. Upon modification, the modifications are automatically distributed to the third nodes using the instance distribution list. Upon receipt, the modifications overwrite the data at the third nodes.

Having described the general operations for information sharing, each of the operations 300–800 will now be described in detail in FIGS. 3–9.

Figure 3:
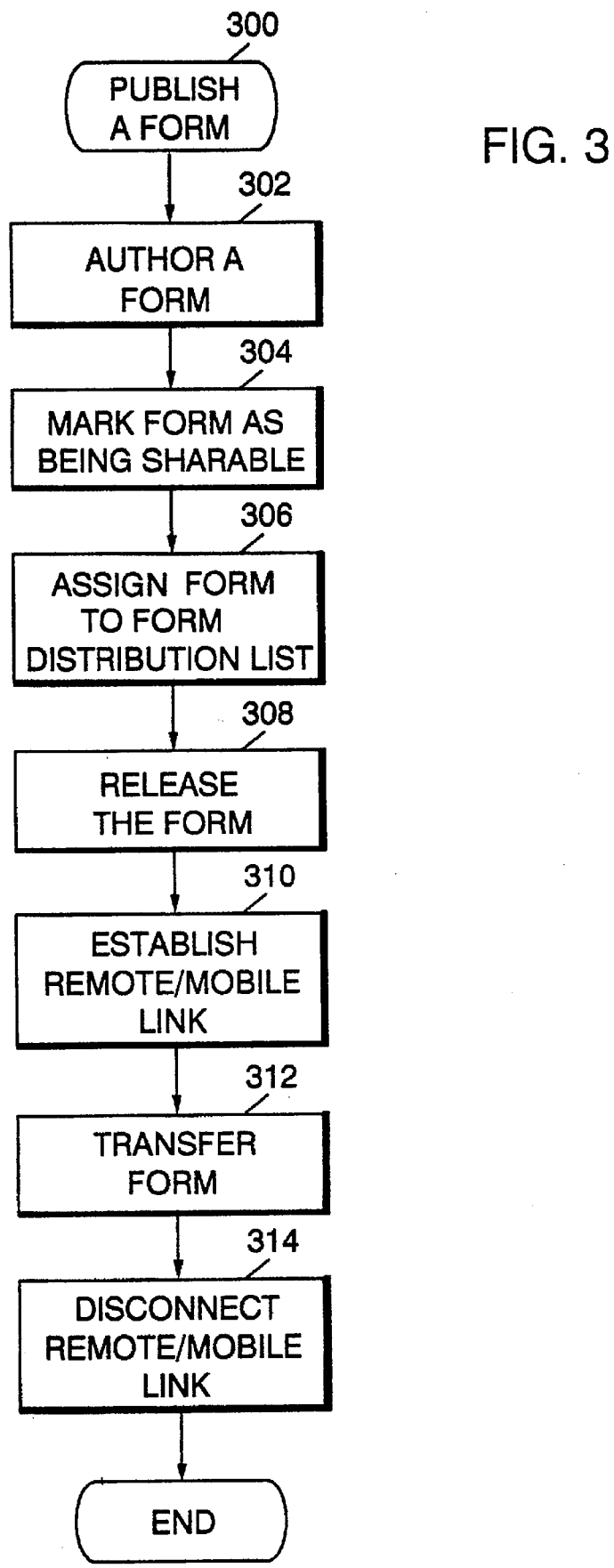
FIG. 3 is a flowchart illustrating operations for publishing a form according to the present invention.

Referring now to FIG. 3, operations for publishing a form (Block 300 of FIG. 2) will now be described. At Block 302, a form is authored. It will be understood by those having skill in the art that the form may be authored at server 110 or may be authored at another computer and placed on server 10. The authoring of a form uses well known form design techniques and systems. Forms may include graphics, fields, text and bitmaps, as well as buttons, scripts, lookups, etc. The design of an electronic form is well known to those skilled in the art and need not be described further herein.

Referring now to Block 304, when the form is placed on the server, it is designated as being shareable so that it can participate in the information sharing system and method according to the present invention. The form may be designated as being shareable using a naming convention or other known technique.

Referring now to Block 306, a form distribution list is assigned to the form to identify users corresponding to first remote/mobile nodes. In order to assign a distribution list, the system administrator selects all users who might have a need to create an instance of the form, from the entire domain of the remote/mobile users in the network.

The form is then released for distribution to the first users at Block 308. Upon release, remote/mobile links are automatically established to the first remote/mobile nodes at Block 310, and the forms are transferred to the first remote/mobile nodes at Block 312. After transfer, the remote/mobile links are disconnected at Block 314. It will be understood that the remote/mobile links may be established for the sole purpose of transferring the form. Alternatively, the form maybe transferred during a remote/mobile session which is periodically established, or established to accomplish other tasks. The establishment of a remote/mobile link between the node and the server is well known to those having skill in the art and need not be described further herein. A preferred system for establishing a remote/mobile link is XcelleNet RemoteWare.

Figure 4:
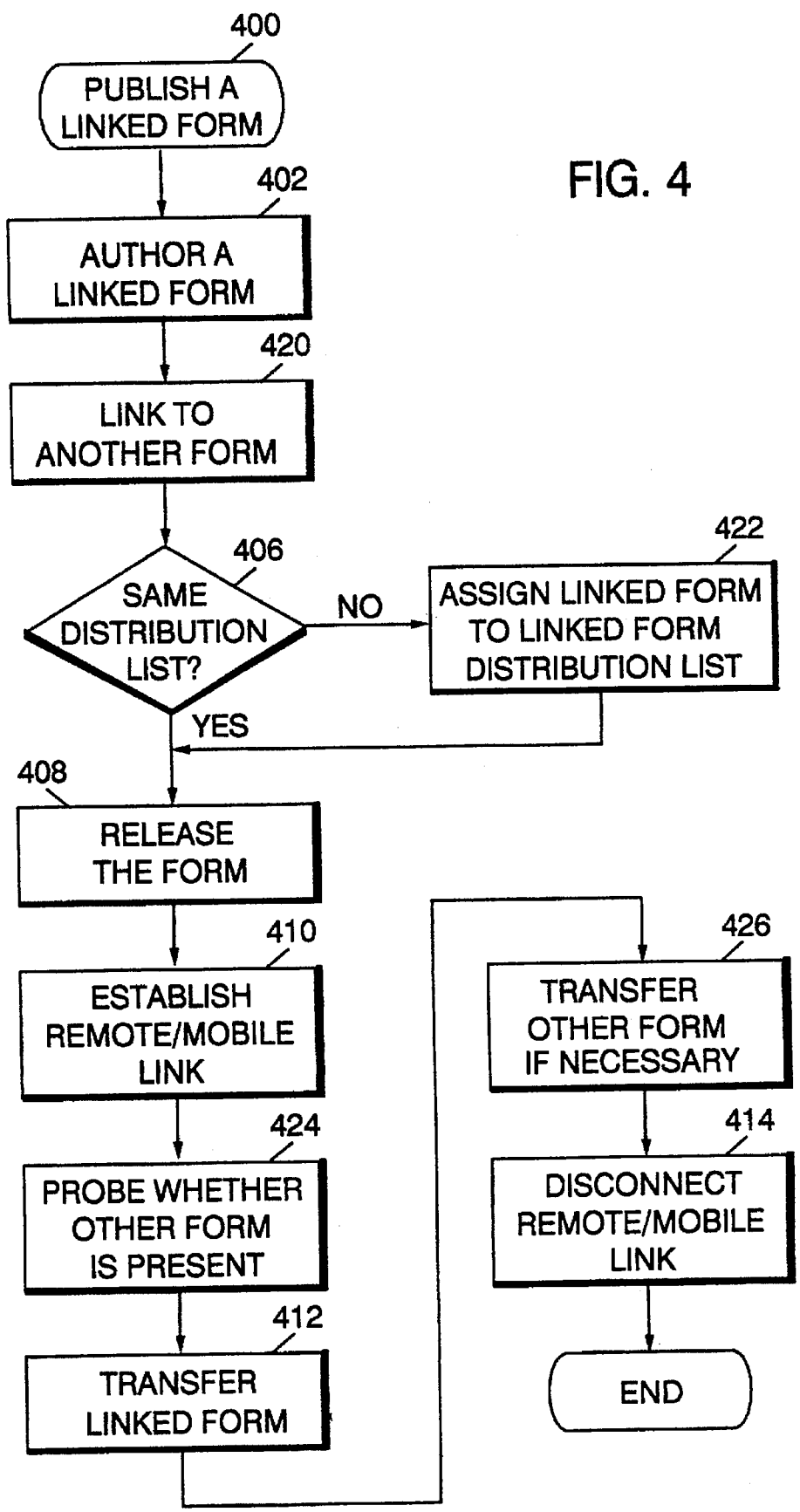
FIG. 4 is a flowchart illustrating operations for publishing a linked form according to the present invention.

Referring now to FIG. 4, operations for publishing a second (linked) form (Block 400 of FIG. 2) will now be described. As already described, a linked form relates to the form described in FIG. 3, now referred to as the first form. The linked form may be published concurrently with or after publication of the first form. At Block 402, the second form is authored similar to Block 302 of FIG. 3. At Block 420, the second information form is linked to the first information form. Information, such as names, addresses or other identifiers, may be automatically transferred from the first information form to the second information form. The second form is also designated as being shareable At Block 406, a decision is made as to whether the same distribution list is used for the linked form as for the first form. Typically, the form distribution list for the first form is also used for the second form. However, the same list need not be used. If the same distribution list is not used, then at Block 422 the linked form is assigned to a linked form distribution list.

At Block 408, the linked form is released similar to Block 308. At Block 410, remote/mobile links are established. The remote/mobile links are established to the first remote/mobile nodes if the same distribution list is used as the original form. Otherwise, remote/mobile links are established with remote/mobile nodes which correspond to users identified in the linked form distribution list. At Block 424, a probe is first made as to whether the first information form is already present at the node. The probe may be made by sending a simple message to the node to search for the presence of a known file at the node. Detailed operations for probing a node will be described in connection with FIG. 9. Then, at Block 412, the second form is transferred, similar to Block 312 of FIG. 3.

At Block 426, the first form is also transferred if the probe indicates that the information form was not present. At Block 414, the remote/mobile link is disconnected, similar to the operation described at Block 314. Accordingly, forms and linked forms are distributed to a distribution list of remote/mobile users who may have a need to use the form.

Referring now to FIG. 5, operations for completing an instance of a form (Block 500 of FIG. 2) will now be described. It will be understood that these operations are performed similarly whether the instance is an instance of an information form or of a linked form. Upon completion of the information in the instance form, the user selects a "share" option at Block 504, indicating that the instance form is to be automatically shared with other interested users rather than being maintained only at the originating users node.

At Block 506, selection is made as to whether the user or the server selects routing. In some cases, such as the distribution of an instance of a customer form, the user may select a department or sales force group to which the instance will be distributed. However, on other cases, such as creation of a new employee profile instance, the institution may decide to whom the new employee information is to be distributed. Accordingly, at Block 508, if the routing is selected by the user, the user assigns an instance distribution list to the instance of the form to identify users corresponding to third remote/mobile nodes. The same distribution list is used for an instance of an information (first) form and for an instance of a linked (second) form, so that an instance of the linked form is automatically distributed to the same users as the instance of the information form. Typically, a selected node from the first nodes, referred to as a second node, will generate the instance of the first form, and another selected node from the first node, referred to as a fourth node, will generate the instance of the second form. Of course, the same node may originate both instances.

At Block 510, a remote/mobile link is established with the server and the completed instance is transferred to the server at Block 512. At Block 516, if the user has selected a distribution list, then the instance distribution list is also transferred to the server. The remote/mobile link is then disconnected.

Figure 6A:
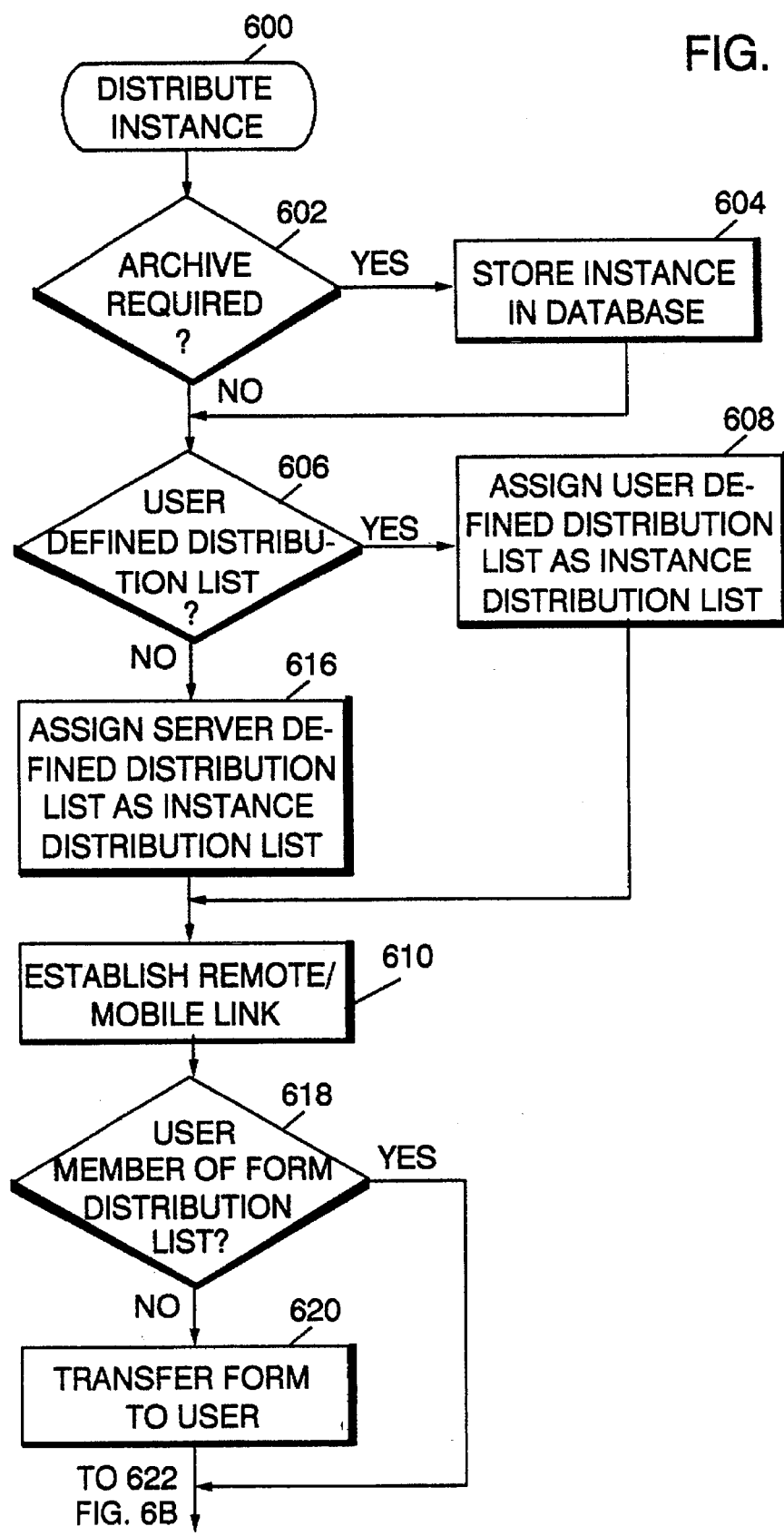
FIG. 6 is a flowchart illustrating operations for distributing an instance according to the present invention.
Figure 6B:
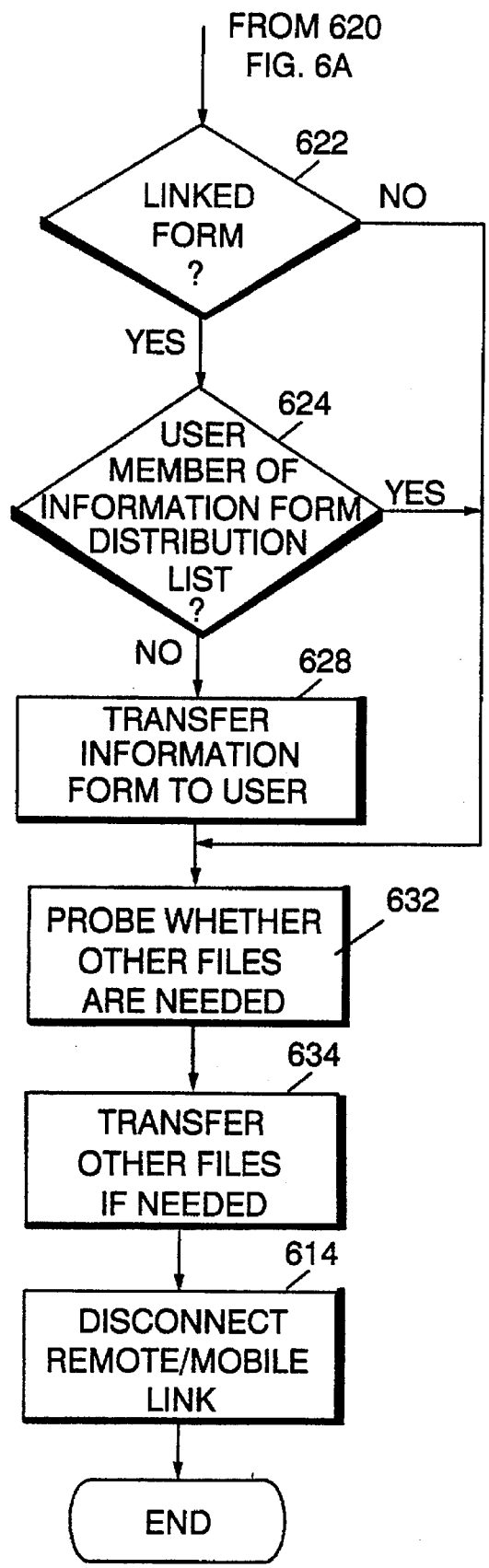

Referring now to FIG. 6, operations for distributing an instance of a form (Block 600 of FIG. 2) will now be described. It will be understood that these operations are performed to distribute instances of information forms to third remote/mobile nodes and instances of linked forms to the third remote/mobile nodes.

At Block 602, a determination is made at the server as to whether archive of the received information is required. If yes, the instance information is stored in database 112 (FIG. 1) or in another database. Storage in the database permits querying of the database using known database querying programs. Accordingly, the database 112 may include a standard database program so that standard query tools may be used.

At Block 606, a test is made as to whether a user-defined instance distribution list was received at Block 516 of FIG. 5. If yes, then the user-defined instance distribution list is assigned as the instance distribution list at Block 608. If not, then the server-defined distribution list is assigned as the instance distribution list at Block 616. Remote/mobile communications links are then established at Block 610 with the third remote/mobile nodes for the information form or for a linked form.

A test is made at Block 618 as to whether the user is a member of the form distribution list. In other words, it is possible that the completed instance of the form is being transferred to a node which has not received the form itself during the original distribution. If this is the case, the form is transferred to the user at Block 620. It will be understood by those having skill in the art that the test at Block 618 may be performed before establishing the remote/mobile link.

At Block 622, a test is made as to whether the form is a linked form. If yes, a test is made at Block 624 as to whether the recipient is a member of the information form distribution list. In other words, it is possible that the user is being supplied with a copy of the linked form in a separate distribution without being supplied with a copy of the information form. If so, then the information form is also transferred to the user at Block 628.

Finally, at Block 632, a probe is made as to whether other files are necessary in order to manipulate the instance which is distributed. If so, the other files are transferred at Block 634. The remote/mobile nodes are then disconnected at Block 614. Detailed operations for probing a node will be described in connection with FIG. 9.

Figure 7:
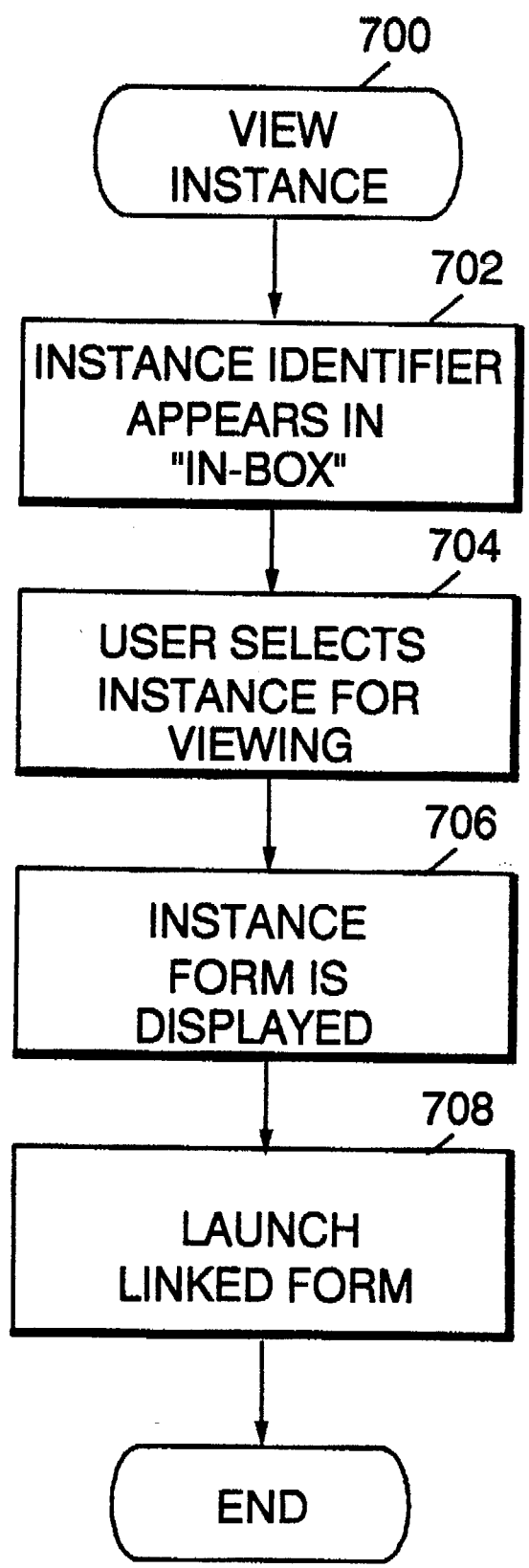
FIG. 7 is a flowchart illustrating operations for viewing an instance according to the present invention.

Referring now to FIG. 7, operations for viewing an instance (Block 700 of FIG. 2) will now be described. Upon receipt of an instance at a third node, an instance identifier appears in the node's in-box at Block 702. The instance identifier may be any kind of message, icon or other indicia to indicate to the user that a new instance has been received. At Block 704, the user selects the instance for viewing, and at Block 706 the instance form is displayed. At Block 708 a linked form may be launched as described above.

Figure 8:
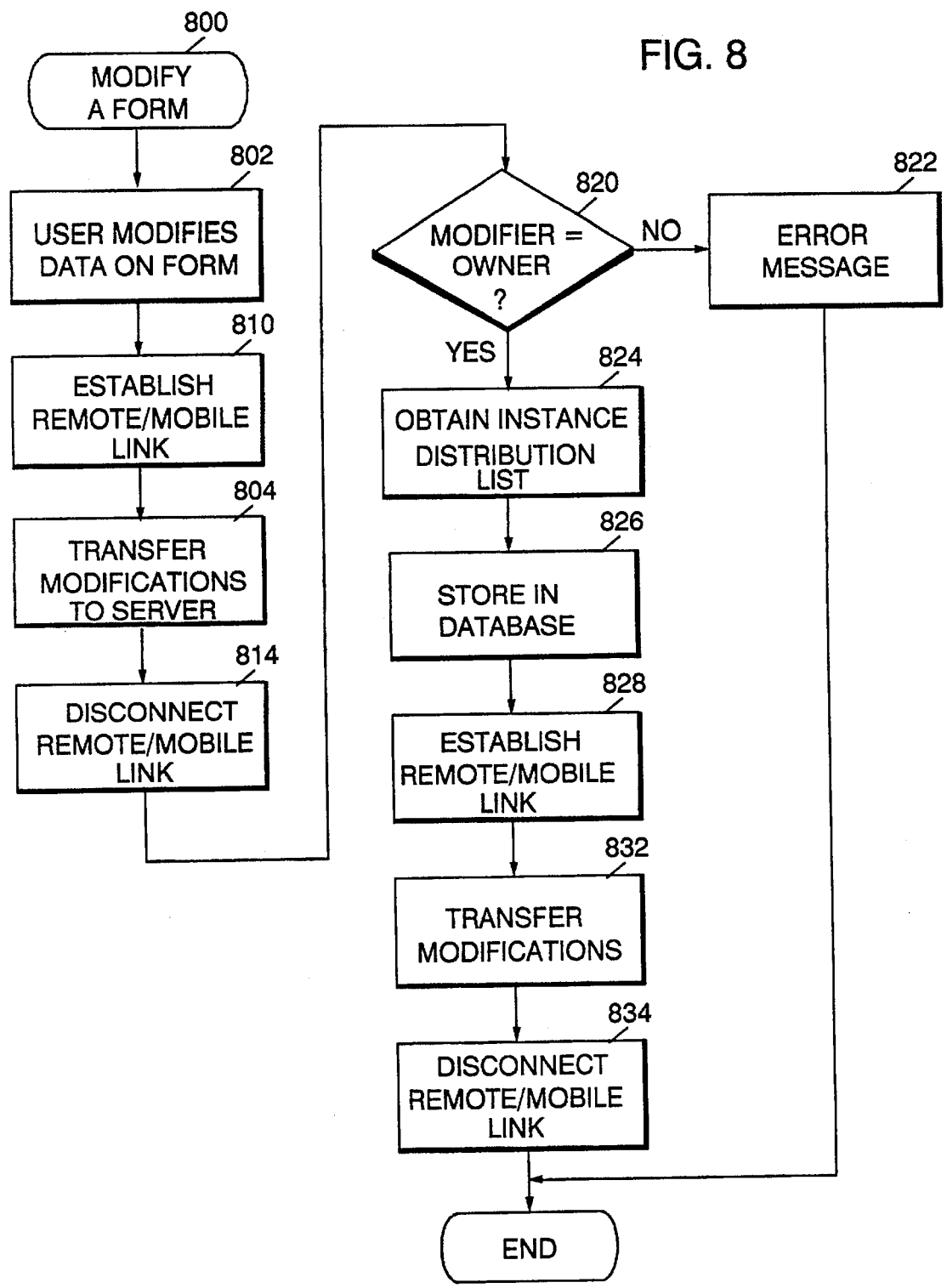
FIG. 8 is a flowchart illustrating operations performed for modifying an instance according to the present invention.

Referring now to FIG. 8, operations for modifying a form (Block 800 of FIG. 2) will now be described. Only the owner of a form, i.e. the originator of the instance of the information form (second node) or linked form (fourth node), may modify the form. Also, only the modifications are automatically shared to thereby decrease the remote/mobile communications time.

At Block 802, in order to modify a form, a owner changes data on a form. For example, a new address or contact point may be provided for the form. At Block 810, a remote/mobile link is established, and at Block 804 the modifications are transferred to the server. The remote/mobile communication link is then disconnected at Block 814.

Once received at the server, a test is made as to whether the user who has modified the form is the owner (originator) of the instance of the form. If not, an error message may be sent at Block 822, informing the modifier that he is not the owner of the form, and that the form can be modified by sending a separate message to the owner of the form. The owner of the form may also be identified.

If, at Block 820, the modifier is the owner, then the instance distribution list for the unmodified instance is obtained at Block 824. The modified data is also stored in the database, if necessary, at Block 826. It will be understood that the modification may be appended to the original data or may automatically replace the original data. At Block 828, remote/mobile communication links are established with the distribution lists of the unmodified instance. At Block 832, the modifications are transferred to these nodes. It will be understood that preferably only the modifications are transferred rather than the entire form. At Block 834, the remote/mobile links are disconnected. The modified form is then displayed as already described in connection with FIG. 7. The modifications are highlighted to make the changes readily apparent to the viewer.

Figure 9:
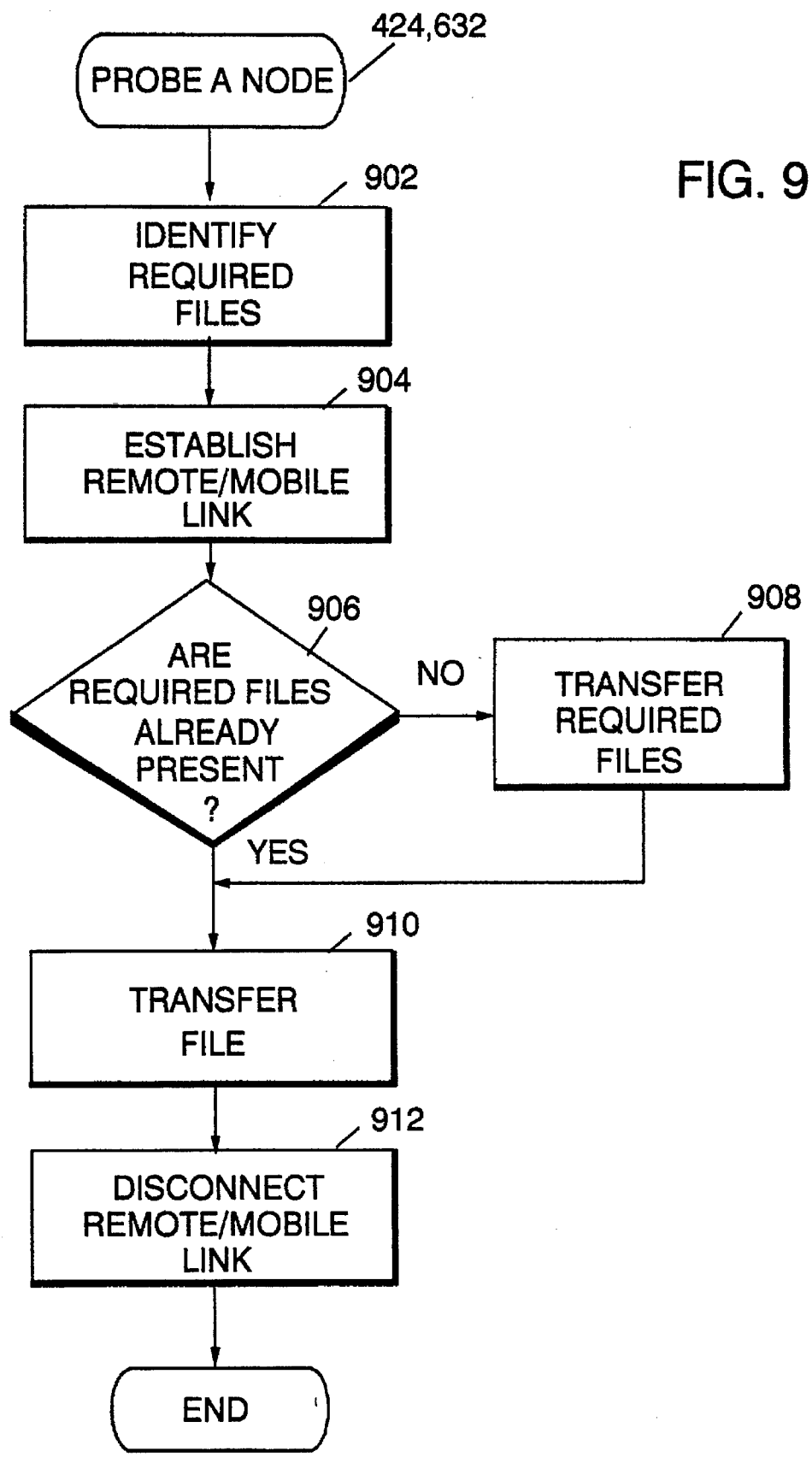
FIG. 9 is a flowchart illustrating operations performed for probing a node according to the present invention.

Referring now to FIG. 9, operations for probing a node (Blocks 424 and 632) will now be described. The probing technique may be used as part of the information sharing process described above. However, the probing technique may also be used prior to any file transfer in a remote/mobile environment. In particular, in contrast with a traditional LAN-based client/server network, and most other computer networks, the identify of all files stored at a remote/mobile node may not be known, because files may be added and/or deleted when the remote/mobile node is not connected to the server. Accordingly, situations may arise where a file is transferred to a node but the file requires other files in order to use the transferred file. Some nodes may include the other files while some nodes may not.

According to the invention, contemporaneous with transferring a file to a node, a probe is made of the node to determine whether or not the other required files already exist at the node. If they do, they are not sent. However, if they do not already exist, they are sent. Accordingly, the probing technique minimizes remote/mobile connection time by (1) only sending files which are not already present at the node; and (2) insuring that a file that is sent will be usable because all other required files will be present.

Referring again to FIG. 9, at Block 902, when transferring a file to a node, required files are also identified. For example, when transferring spreadsheet data, the files for the spreadsheet program itself are identified. As another example, when transferring instance data for a form, the file containing the form shell is identified.

At Block 904, a remote/mobile link is established and a determination is made at Block 906 as to whether the required files are already present at the node. The determination may be made by sending a query to the node as to whether a particular file name is present at the node. If not, then at Block 908, the required files are transferred. At Block 910, the file itself is transferred. At Block 912, the remote/mobile links are disconnected. It will be understood by those having skill in the art that the operations of Blocks 906, 908 and 910 may occur during separate remote/mobile communications. Moreover, the file itself may be transferred before the required file. Accordingly, it is insured that the required files exist at the node, so that a transferred file may be utilized in its intended manner.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed:

1. A method for automatically sharing information among a plurality of remote/mobile data processing nodes which are temporarily and intermittently linked to a data processing server for communication therebetween, said automatic information sharing method comprising the steps of:

placing an information form for entering information from a user at a remote/mobile data processing node, on said server;

identifying said form as being sharable;

assigning a form distribution list to said form to identify users corresponding to first remote/mobile nodes;

establishing a remote/mobile communications link to at least one node of said first remote/mobile nodes;

automatically transferring said form to said at least one node of said first remote/mobile nodes, in response to establishment of the remote/mobile communications link to said at least one node of said first remote/mobile nodes;

disconnecting said remote/mobile communications link from said at least one node of said first remote/mobile nodes;

accepting user entry of information into said form at a second remote mobile node selected from said first remote/mobile nodes to thereby create an instance of said form at said second remote/mobile node;

assigning an instance distribution list to said instance of said form to identify users corresponding to third remote/mobile nodes selected from said first remote/mobile nodes;

establishing a remote/mobile communications link between said second node and said server;

automatically transferring said instance of said form to said server, in response to establishment of the remote/mobile link between said second node and said server;

disconnecting said remote/mobile communications link between said second node and said server;

establishing a remote/mobile communications link between said server and at least one node of said third remote/mobile nodes;

automatically transferring said instance from said server to said at least one node of said third remote/mobile nodes, in response to establishment of the remote/mobile link between said server and said at least one node of said third remote/mobile nodes; and disconnecting said remote/mobile communications links between said server and said at least one node of said third remote/mobile nodes.

2. An automatic information sharing method according to claim 1 further comprising the steps of:

placing a second information form for entering information from a user at a remote/mobile data processing node, on said server;

linking said second information form to said information form;

assigning said form distribution list to said second form to identify said users corresponding to first remote/mobile nodes;

establishing a remote/mobile communications link to at least one node of said first remote/mobile nodes;

automatically transferring said second form to said at least one node of said first remote/mobile nodes, in response to establishment of the remote/mobile communications link to said at least one node of said first remote/mobile nodes;

disconnecting said remote/mobile communications link from said at least one node of said first remote/mobile nodes;

accepting user entry of information into said second form at a fourth remote mobile node selected from said third remote/mobile nodes to thereby create an instance of said second form at said fourth remote/mobile node;

establishing a remote/mobile communications link between said fourth remote/mobile node and said server;

automatically transferring said instance of said second form to said server, in response to establishment of said remote/mobile communications link between said fourth remote/mobile node and said server;

disconnecting said remote/mobile communications link between said fourth remote/mobile node and said server;

establishing remote/mobile communications links between said server and at least one node of said third remote/mobile nodes;

automatically transferring said instance of said second form from said server to said at least one node of said third remote/mobile nodes, in response to establishment of the remote/mobile communications link between said server and said at least one node of said third remote/mobile nodes; and disconnecting said remote/mobile communications links between said server and said at least one node of said third remote/mobile nodes.

3. An automatic information sharing method according to claim 1:

wherein said step of assigning a form distribution list to said form to identify users corresponding to first remote/mobile nodes is performed at said server;

wherein said step of assigning an instance distribution list to said instance of said form to identify users corresponding to third remote/mobile nodes is performed at said second node; and wherein said step of transferring said instance of said form to said server further comprises the step of transferring said instance distribution list to said server.

4. An automatic information sharing method according to claim 2 wherein said step of creating an instance of said second form at a fourth remote/mobile node comprises the steps of:

viewing said instance of said form at said fourth remote/mobile node;

launching said instance of said second form at said fourth remote/mobile node; and completing said instance of said second form at said fourth remote/mobile node.

5. An automatic information sharing method according to claim 1 further comprising the steps of:

modifying said instance of said form at said second remote/mobile node;

transmitting the modifications to said server; and transmitting the modifications from said server to said third remote/mobile nodes.

6. An automatic information sharing method according to claim 5 further comprising the step of:

replacing corresponding information in said instance of said form at said third remote/mobile nodes with the modifications.

7. An automatic information sharing method according to claim 5 wherein said step of transmitting the modifications from said server to said third remote/mobile nodes comprises the steps of:

determining whether said modifications originated from said second remote/mobile node; and transmitting the modifications to said third remote/mobile nodes only if the modifications originated from said second remote/mobile node.

8. An automatic information sharing method according to claim 2 further comprising the steps of:

modifying said instance of said second form at said fourth remote/mobile node;

transmitting the modifications to said server; and transmitting the modifications from said server to said third remote/mobile nodes.

9. An automatic information sharing method according to claim 8 further comprising the step of:

replacing corresponding information in said instance of said second form at said third remote/mobile nodes with the modifications.

10. An automatic information sharing method according to claim 8 wherein said step of automatically transmitting the modifications from said server to said third remote/mobile nodes comprises the steps of:

determining whether said modifications originated from said fourth remote/mobile node; and transmitting the modifications to said third remote/mobile nodes only if the modifications originated from said fourth remote/mobile node.

11. An automatic information sharing method according to claim 1 wherein said step of automatically transferring said form to at least one node of said first remote/mobile nodes comprises the steps of:

identifying files which are required in order to use said form;

probing said at least one node of said first nodes in order to determine if the identified files are present at said at least node one of said first remote/mobile nodes; and automatically transferring the identified files from said server to said at least one node of said first remote/mobile nodes if the identified files are not present at said at least one node of said first remote/mobile nodes.

12. A method for automatically sharing information among a plurality of remote/mobile data processing nodes which are temporarily and intermittently linked to a data processing server for communication therebetween, said automatic information sharing method comprising the steps of:

placing an information form for entering information from a user at a remote/mobile data processing node, on said server;

identifying said form as being sharable;

assigning a form distribution list to said form to identify users corresponding to first remote/mobile nodes;

establishing a remote/mobile communications link to at least one node of said first remote/mobile nodes;

automatically transferring said form to said at least one node of said first remote/mobile nodes;

disconnecting said remote/mobile communications link from said at least one node of said first remote/mobile nodes;

accepting user entry of information into said form at a second remote/mobile node selected from said first remote/mobile nodes to thereby create an instance of said form at said second remote/mobile node;

assigning an instance distribution list to said instance of said form to identify users corresponding to third remote/mobile nodes selected from said first remote/mobile nodes;

establishing a remote/mobile communications link between said second node and said server;

automatically transferring said instance of said form to said server, in response to establishment of the remote/mobile communications link between said second node and said server;

disconnecting said remote/mobile communications link between said second node and said server;

establishing a remote/mobile communications link between said server and at least one node of said third remote/mobile nodes;

automatically transferring said instance from said server to said at least one node of said third remote/mobile nodes, in response to establishment of the remote/mobile communications link between said server and said at least one node of said third remote/mobile nodes;

disconnecting said remote/mobile communications links between said server and said at least one node of said third remote/mobile nodes;

modifying said instance of said form at said second remote/mobile node;

establishing a remote/mobile communications link between said second node and said server;

transmitting the modifications to said server;

disconnecting said remote/mobile communications link between said second node and said server;

establishing a remote/mobile communications link between said server and at least one node of said third remote/mobile nodes;

automatically transmitting the modifications from said server to said at least one node of said third remote/mobile nodes, in response to establishment of the remote/mobile communications link between said server and said at least one node of said third remote/mobile nodes; and disconnecting said remote/mobile communications links between said server and said at least one node of said third remote/mobile nodes.

13. An automatic information sharing method according to claim 12 further comprising the steps of:

placing a second information form for entering information from a user at a remote/mobile data processing node, on said server;

linking said second information form to said information form;

assigning said form distribution list to said second form to identify said users corresponding to first remote/mobile nodes;

establishing a remote/mobile communications link to at least one node of said first remote/mobile nodes;

automatically transferring said second form to said at least one node of said first remote/mobile nodes, in response to establishment of the communications link to said at least one node of said first remote/mobile nodes;

disconnecting said remote/mobile communications link from said at least one node of said first remote/mobile nodes;

accepting user entry of information into said second form at a fourth remote/mobile node selected from said third remote/mobile nodes to thereby create an instance of said second form at said fourth remote/mobile node;

establishing a remote/mobile communications link between said fourth remote/mobile node and said server;

automatically transferring said instance of said second form to said server, in response to establishment of the remote/mobile communications link between said fourth remote/mobile node and said server;

disconnecting said remote/mobile communications link between said fourth remote/mobile node and said server;

establishing a remote/mobile communications link between said server and at least one node of said third remote/mobile nodes;

automatically transferring said instance of said second form from said server to said at least one node of said third remote/mobile nodes, in response to establishment of the remote/mobile communications link between said server and said at least one node of said third remote/mobile nodes; and disconnecting said remote/mobile communications link between said server and said at least one node of said third remote/mobile nodes.

14. An automatic information sharing method according to claim 12:

wherein said step of assigning a form distribution list to said form to identify users corresponding to first remote/mobile nodes is performed at said server;

wherein said step of assigning an instance distribution list to said instance of said form to identify users corresponding to third remote/mobile nodes is performed at said second node; and wherein said step of transferring said instance of said form to said server further comprises the step of transferring said instance distribution list to said server.

15. An automatic information sharing method according to claim 13 wherein said step of creating an instance of said second form at a fourth remote/mobile node comprises the steps of:

viewing said instance of said form at said fourth remote/mobile node;

launching said instance of said second form at said fourth remote/mobile node; and completing said instance of said second form at said fourth remote/mobile node.

16. An automatic information sharing method according to claim 12 further comprising the step of:

replacing corresponding information in said instance of said form at said at least one node of said third remote/mobile nodes with the modifications.

17. An automatic information sharing method according to claim 12 wherein said step of automatically transmitting the modifications from said server to said at least one node of said third remote/mobile nodes comprises the steps of:

determining whether said modifications originated from said second remote/mobile node; and transmitting the modifications to said at least one node of said third remote/mobile nodes only if the modifications originated from said second remote/mobile node.

18. An automatic information sharing method according to claim 13 further comprising the steps of:

modifying said instance of said second form at said fourth remote/mobile node;

transmitting the modifications to said server; and transmitting the modifications from said server to said third remote/mobile nodes.

19. An automatic information sharing method according to claim 18 further comprising the step of:

replacing corresponding information in said instance of said second form at said third remote/mobile nodes with the modifications.

20. An automatic information sharing method according to claim 18 wherein said step of automatically transmitting the modifications from said server to said third remote/mobile nodes comprises the steps of:

determining whether said modifications originated from said fourth remote/mobile node; and transmitting the modifications to said third remote/mobile nodes only if the modifications originated from said fourth remote/mobile node.

21. An automatic information sharing method according to claim 12 wherein said step of transferring said form to at least one of said first remote/mobile nodes comprises the steps of:

identifying files which are required in order to use said form;

probing said at least one of said first nodes in order to determine if the identified files are present at said at least one of said first remote/mobile nodes; and transferring the identified files from said server to said at least one of said first remote/mobile nodes if the identified files are not present at said at least one of said first remote/mobile nodes.

22. A computer program storage device which tangibly embodies a program of instructions executable on a plurality of remote/mobile data processing nodes which are temporarily and intermittently linked to a data processing server for communication therebetween, to perform a method for automatically sharing information among the plurality of remote/mobile data processing nodes which are temporarily and intermittently linked to the data processing server for communication therebetween, said automatic information sharing method comprising the steps of:

placing an information form for entering information from a user at a remote/mobile data processing node, on said server;

identifying said form as being sharable;

assigning a form distribution list to said form to identify users corresponding to first remote/mobile nodes;

establishing a remote/mobile communications link to at least one node of said first remote/mobile nodes;

automatically transferring said form to said at least one node of said first remote/mobile nodes, in response to establishment of the remote/mobile communications link to said at least one node of said first remote/mobile nodes;

disconnecting said remote/mobile communications link from said at least one node of said first remote/mobile nodes;

accepting user entry of information into said form at a second remote mobile node selected from said first remote/mobile nodes to thereby create an instance of said form at said second remote/mobile node;

assigning an instance distribution list to said instance of said form to identify users corresponding to third remote/mobile nodes selected from said first remote/mobile nodes;

establishing a remote/mobile communications link between said second node and said server;

automatically transferring said instance of said form to said server, in response to establishment of the remote/mobile link between said second node and said server;

disconnecting said remote/mobile communications link between said second node and said server;

establishing a remote/mobile communications link between said server and at least one node of said third remote/mobile nodes;

automatically transferring said instance from said server to said at least one node of said third remote/mobile nodes, in response to establishment of the remote/mobile link between said server and said at least one node of said third remote/mobile nodes; and disconnecting said remote/mobile communications links between said server and said at least one node of said third remote/mobile nodes.

23. A computer program storage device according to claim 2 wherein said method further comprises the steps of:

placing a second information form for entering information from a user at a remote/mobile data processing node, on said server;

linking said second information form to said information form;

assigning said form distribution list to said second form to identify said users corresponding to first remote/mobile nodes;

establishing a remote/mobile communications link to at least one node of said first remote/mobile nodes;

automatically transferring said second form to said at least one node of said first remote/mobile nodes, in response to establishment of the remote/mobile communications link to said at least one node of said first remote/mobile nodes;

disconnecting said remote/mobile communications link from said at least one node of said first remote/mobile nodes;

accepting user entry of information into said second form at a fourth remote mobile node selected from said third remote/mobile nodes to thereby create an instance of said second format said fourth remote/mobile node;

establishing a remote/mobile communications link between said fourth remote/mobile node and said server;

automatically transferring said instance of said second form to said server, in response to establishment of said remote/mobile communications link between said fourth remote/mobile node and said server;

disconnecting said remote/mobile communications link between said fourth remote/mobile node and said server;

establishing remote/mobile communications links between said server and at least one node of said third remote/mobile nodes;

automatically transferring said instance of said second form from said server to said at least one node of said third remote/mobile nodes, in response to establishment of the remote/mobile communications link between said server and said at least one node of said third remote/mobile nodes; and disconnecting said remote/mobile communications links between said server and said at least one node of said third remote/mobile nodes.

24. A computer program storage device according to claim 22:

wherein said step of assigning a form distribution list to said form to identify users corresponding to first remote/mobile nodes is performed at said server;

wherein said step of assigning an instance distribution list to said instance of said form to identify users corresponding to third remote/mobile nodes is performed at said second node; and wherein said step of transferring said instance of said form to said server further comprises the step of transferring said instance distribution list to said server.

25. A computer program storage device according to claim 23 wherein said step of creating an instance of said second form at a fourth remote/mobile node comprises the steps of:

viewing said instance of said form at said fourth remote/mobile node;

launching said instance of said second form at said fourth remote/mobile node; and completing said instance of said second form at said fourth remote/mobile node.

26. A computer program storage device according to claim 22 wherein said method further comprises the steps of:

modifying said instance of said form at said second remote/mobile node;

transmitting the modifications to said server; and transmitting the modifications from said server to said third remote/mobile nodes.

27. A computer program storage device according to claim 26 wherein said method further comprises the step of:

replacing corresponding information in said instance of said form at said third remote/mobile nodes with the modifications.

28. A computer program storage device according to claim 26 wherein said step of transmitting the modifications from said server to said third remote/mobile nodes comprises the steps of:

determining whether said modifications originated from said second remote/mobile node; and transmitting the modifications to said third remote/mobile nodes only if the modifications originated from said second remote/mobile node.

29. A computer program storage device according to claim 23 wherein said method further comprises the steps of:

modifying said instance of said second form at said fourth remote/mobile node;

transmitting the modifications to said server; and transmitting the modifications from said server to said third remote/mobile nodes.

30. A computer program storage device according to claim 29 wherein said method further comprises the step of:

replacing corresponding information in said instance of said second form at said third remote/mobile nodes with the modifications.

31. A computer program storage device according to claim 29 wherein said step of automatically transmitting the modifications from said server to said third remote/mobile nodes comprises the steps of:

determining whether said modifications originated from said fourth remote/mobile node; and transmitting the modifications to said third remote/mobile nodes only if the modifications originated from said fourth remote/mobile node.

32. A computer program storage device according to claim 22 wherein said step of automatically transferring said form to at least one node of said first remote/mobile nodes comprises the steps of:

identifying files which are required in order to use said form;

probing said at least one node of said first nodes in order to determine if the identified files are present at said at least node one of said first remote/mobile nodes; and automatically transferring the identified files from said server to said at least one node of said first remote/mobile nodes if the identified files are not present at said at least one node of said first remote/mobile nodes.

33. A computer program storage device which tangibly embodies a program of instructions executable on a plurality of remote/mobile data processing nodes which are temporarily and intermittently linked to a data processing server for communication therebetween, to perform a method for automatically sharing information among the plurality of remote/mobile data processing nodes which are temporarily and intermittently linked to the data processing server for communication therebetween, said automatic information sharing method comprising the steps of:

placing an information form for entering information from a user at a remote/mobile data processing node, on said server;

identifying said form as being sharable;

assigning a form distribution list to said form to identify users corresponding to first remote/mobile nodes;

establishing a remote/mobile communications link to at least one node of said first remote/mobile nodes;

automatically transferring said form to said at least one node of said first remote/mobile nodes;

disconnecting said remote/mobile communications link from said at least one node of said first remote/mobile nodes;

accepting user entry of information into said form at a second remote/mobile node selected from said first remote/mobile nodes to thereby create an instance of said form at said second remote/mobile node;

assigning an instance distribution list to said instance of said form to identify users corresponding to third remote/mobile nodes selected from said first remote/mobile nodes;

establishing a remote/mobile communications link between said second node and said server;

automatically transferring said instance of said form to said server, in response to establishment of the remote/mobile communications link between said second node and said server;

disconnecting said remote/mobile communications link between said second node and said server;

establishing a remote/mobile communications link between said server and at least one node of said third remote/mobile nodes;

automatically transferring said instance from said server to said at least one node of said third remote/mobile nodes, in response to establishment of the remote/mobile communications link between said server and said at least one node of said third remote/mobile nodes;

disconnecting said remote/mobile communications links between said server and said at least one node of said third remote/mobile nodes;

modifying said instance of said form at said second remote/mobile node;

establishing a remote/mobile communications link between said second node and said server;

transmitting the modifications to said server;

disconnecting said remote/mobile communications link between said second node and said server;

establishing a remote/mobile communications link between said server and at least one node of said third remote/mobile nodes;

automatically transmitting the modifications from said server to said at least one node of said third remote/mobile nodes, in response to establishment of the remote/mobile communications link between said server and said at least one node of said third remote/mobile nodes; and disconnecting said remote/mobile communications links between said server and said at least one node of said third remote/mobile nodes.

34. A computer program storage device according to claim 33 wherein said method further comprises the steps of:

placing a second information form for entering information from a user at a remote/mobile data processing node, on said server;

linking said second information form to said information form;

assigning said form distribution list to said second form to identify said users corresponding to first remote/mobile nodes;

establishing a remote/mobile communications link to at least one node of said first remote/mobile nodes;

automatically transferring said second form to said at least one node of said first remote/mobile nodes, in response to establishment of the communications link to said at least one node of said first remote/mobile nodes;

disconnecting said remote/mobile communications link from said at least one node of said first remote/mobile nodes;

accepting user entry of information into said second form at a fourth remote/mobile node selected from said third remote/mobile nodes to thereby create an instance of said second form at said fourth remote/mobile node;

establishing a remote/mobile communications link between said fourth remote/mobile node and said server;

automatically transferring said instance of said second form to said server, in response to establishment of the remote/mobile communications link between said fourth remote/mobile node and said server;

disconnecting said remote/mobile communications link between said fourth remote/mobile node and said server;

establishing a remote/mobile communications link between said server and at least one node of said third remote/mobile nodes;

automatically transferring said instance of said second form from said server to said at least one node of said third remote/mobile nodes, in response to establishment of the remote/mobile communications link between said server and said at least one node of said third remote/mobile nodes; and disconnecting said remote/mobile communications link between said server and said at least one node of said third remote/mobile nodes.

35. A computer program storage device according to claim 33:

wherein said step of assigning a form distribution list to said form to identify users corresponding to first remote/mobile nodes is performed at said server;

wherein said step of assigning an instance distribution list to said instance of said form to identify users corresponding to third remote/mobile nodes is performed at said second node; and wherein said step of transferring said instance of said form to said server further comprises the step of transferring said instance distribution list to said server.

36. A computer program storage device according to claim 34 wherein said step of creating an instance of said second form at a fourth remote/mobile node comprises the steps of:

viewing said instance of said form at said fourth remote/mobile node;

launching said instance of said second form at said fourth remote/mobile node; and completing said instance of said second form at said fourth remote/mobile node.

37. A computer program storage device according to claim 33 wherein said method further comprises the step of:

replacing corresponding information in said instance of said form at said at least one node of said third remote/mobile nodes with the modifications.

38. A computer program storage device according to claim 33 wherein said step of automatically transmitting the modifications from said server to said at least one node of said third remote/mobile nodes comprises the steps of:

determining whether said modifications originated from said second remote/mobile node; and transmitting the modifications to said at least one node of said third remote/mobile nodes only if the modifications originated from said second remote/mobile node.

39. A computer program storage device according to claim 34 wherein said method further comprises the steps of:

modifying said instance of said second form at said fourth remote/mobile node;

transmitting the modifications to said server; and transmitting the modifications from said server to said third remote/mobile nodes.

40. A computer program storage device according to claim 39 wherein said method further comprises the step of:

replacing corresponding information in said instance of said second form at said third remote/mobile nodes with the modifications.

41. A computer program storage device according to claim 39 wherein said step of automatically transmitting the modifications from said server to said third remote/mobile nodes comprises the steps of:

determining whether said modifications originated from said fourth remote/mobile node; and transmitting the modifications to said third remote/mobile nodes only if the modifications originated from said fourth remote/mobile node.

42. A computer program storage device according to claim 33 wherein said step of transferring said form to at least one of said first remote/mobile nodes comprises the steps of:

identifying files which are required in order to use said form;

probing said at least one of said first nodes in order to determine if the identified files are present at said at least one of said first remote/mobile nodes; and transferring the identified files from said server to said at least one of said first remote/mobile nodes if the identified files are not present at said at least one of said first remote/mobile nodes.

* * * * *